United States Patent [19]

Bailey

[11] Patent Number: 4,510,139

[45] Date of Patent: Apr. 9, 1985

[54] SUBSTITUTED AMINOBENZAMIDES AND THEIR USE AS AGENTS WHICH INHIBIT LIPOXYGENASE ACTIVITY

[75] Inventor: Denis M. Bailey, East Greenbush, N.Y.

[73] Assignee: Sterling Drug Inc., New York, N.Y.

[21] Appl. No.: 568,870

[22] Filed: Jan. 6, 1984

[51] Int. Cl.$^3$ .................. C07D 295/18; C07C 103/22; C07C 103/29; C07C 103/85

[52] U.S. Cl. .................................... 514/234; 544/165; 546/226; 548/539; 564/163; 564/167; 514/329; 514/426; 514/826

[58] Field of Search ........................ 546/226; 544/165; 548/539; 564/163, 167; 424/324, 248.56, 274, 267

[56] References Cited

U.S. PATENT DOCUMENTS 4,093,734  6/1978  Kruger et al. ...................... 546/226

OTHER PUBLICATIONS

Dong Han Kim, J. Heterocyclic Chem., vol. 18, (1981), pp. 1389–1392.
H. Brockmann et al., Chem. Ber., vol. 104, (1971), pp. 2751–2771.
Chatterjee et al., J. Indian Chem. Soc., 46, 103–108, (1969).
Chen et al., J. Med. Chem., 21, 868–874, (1978).
Juby et al., J. Med. Chem., 11, 111–117, (1968).
Cain et al., J. Med. Chem., 18, 1110–1117, (1975).
G. Ege, Chem. Ber., 101, 3079–3088, (1968).
Legrand et al., Bull. Soc. Chim., France, 1973, (pt. 2), 1665–1667.
Legrand et al., Bull. Soc. Chim., France, 1975, (pt. 2), 1415–1418.
Iwao et al., J. Am. Chem. Soc., 104, 5531–5533, (1982).

Primary Examiner—Norma S. Milestone
Attorney, Agent, or Firm—Thomas L. Johnson; B. Woodrow Wyatt; Paul E. Dupont

[57] ABSTRACT

Novel 2-(hydroxyphenylamino)benzamides and oxidation products thereof, useful as inhibitors of lipoxygenase, are of the formulas

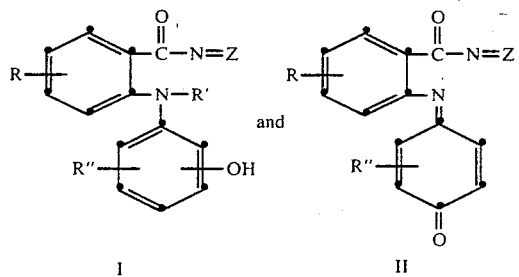

wherein R is hydrogen, lower-alkyl, halo or lower-alkoxy; R' is hydrogen or lower-alkyl; R'' is hydrogen, lower-alkyl or halo; and N=Z is amino or substituted amino. The compounds of Formula I are prepared by de-etherification of the corresponding alkyl or benzyl ethers; and the compounds of Formula II are prepared by oxidation of the compounds of Formula I where R' is hydrogen and OH is in the 4-position.

18 Claims, No Drawings

SUBSTITUTED AMINOBENZAMIDES AND THEIR USE AS AGENTS WHICH INHIBIT LIPOXYGENASE ACTIVITY

BACKGROUND OF THE INVENTION (1) Field of the Invention

The present invention relates to novel 2-(hydroxyphenylamino)benzamides, processes for the preparation thereof, and the use of said amides as agents which inhibit lipoxygenase activity.

(2) Information Disclosure Statement

Juby et al., J. Med. Chem. 11, 111 (1968) disclose the preparation of 2-(phenylamino)benzamide as a chemical intermediate.

Cain et al., J. Med. Chem. 18, 1110 (1975) disclose 1-[2-(3-trifluoromethylphenylamino)benzoyl]piperidine of the formula:

as a chemical intermediate.

G. Ege, Chem. Ber. 101, 3079 (1968) discloses 4-[2-(phenylamino)benzoyl]morpholine of the formula:

as a new chemical compound without any disclosure of utility therefor.

Legrand et al., Bull. Soc. Chim. France 1973 (pt. 2), 1665–7; and 1975 (pt. 2), 1415–18, disclose N-ethyl-2-[(4-methoxyphenyl)amino]benzamide and 4-chloro-2-[(4-methoxyphenyl)amino]-N-phenylbenzamide of the formulas:

as new chemical compounds and intermediates.

Iwao et al., J. Am. Chem. Soc. 104, 5531-3 (1982) disclose 2-methoxy-6-[(3-methoxyphenyl)amino]-N,N-dimethylbenzamide of the formula:

as a chemical intermediate.

Chatterjee et al., J. Indian Chem. Soc. 46, 103–8 (1969) discloses 2-(4-methoxyphenylamino)benzamide as a chemical intermediate.

Chen et al., J. Med. Chem. 21, 868–74 (1978) discloses 4-chloro-2-(3-methoxyphenylamino)-N,N-dimethylbenzamide of the formula:

as a chemical intermediate.

SUMMARY OF THE INVENTION

In a product aspect, the invention relates to compounds of the formulas

I and II wherein:

R is hydrogen, lower-alkyl, halo or lower-alkoxy;

R' is hydrogen or lower-alkyl;

R" is hydrogen, lower-alkyl or halo; and

N=Z is a member of the group consisting of amino, alkylamino having from one to four carbon atoms, dialkylamino having from two to eight carbon atoms, benzylamino, N-benzyl-N-alkylamino having from eight to ten carbon atoms, 5- or 6-ring-membered cycloalkylamino having from five to eight carbon atoms, 1-pyrrolidinyl, 1-piperidinyl, 4-morpholinyl, and lower-alkylated derivatives of said heterocyclic members.

In a further product aspect, the invention relates to compounds of the formula

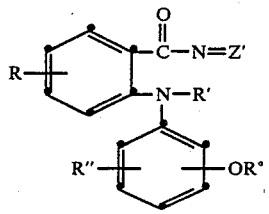

wherein:
R is hydrogen, lower-alkyl, halo or lower-alkoxy;
R' is hydrogen or lower-alkyl;
R" is hydrogen, lower-alkyl or halo;
R° is (a) benzyl or (b) lower-alkyl when R is other than lower-alkoxy; and
N=Z' is a member of the group consisting of benzylamino, N-benzyl-N-alkylamino having from eight to ten carbon atoms, 5- or 6-ring-membered cycloalkylamino having from five to eight carbon atoms, 1-pyrrolidinyl, 1-piperidinyl, 4-morpholinyl, and lower-alkylated derivatives of said heterocyclic members.

In a still further product aspect, the invention relates to compositions for inhibiting lipoxygenase activity, including prevention and treatment of allergic asthma, which comprise a pharmacologically effective amount of a compound of Formula I or II together with one or more pharmaceutically acceptable excipients or diluents.

In a process aspect, the invention relates to a process for preparing a compound of Formula I which comprises de-etherifying a compound of the formula

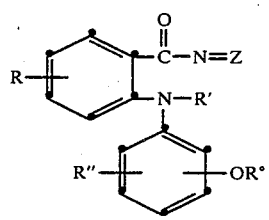

wherein R, R', R" and N=Z have the meanings given above, and R° is lower-alkyl or benzyl, by a method selected from:
(a) catalytically hydrogenating a compound where R° is benzyl; and
(b) treating a compound where R° is benzyl or lower-alkyl and R is other than lower-alkoxy with a strong protonic acid or a Lewis acid.

In a further process aspect, the invention relates to a process for preparing a compound of Formula II which comprises reacting a compound of Formula I where R' is hydrogen with an oxidizing agent capable of converting para-aminophenols to the corresponding 4-imino-2,5-cyclohexadien-1-ones.

In a still further process aspect, the invention relates to a method for inhibiting lipoxygenase activity, including prevention or treatment of allergic asthma, in a mammal which comprises administering to said mammal a pharmacologically effective amount of a compound of Formula I or II together with one or more pharmaceutically acceptable excipients or diluents.

DETAILED DESCRIPTION INCLUSIVE OF PREFERRED EMBODIMENTS

In the foregoing Formulas I-IV, the variables R, R', R" and R° when they stand for lower-alkyl or lower-alkoxy include such groups containing from one to three carbon atoms; and when R or R" stands for halo, it can be any of the common halogens, fluorine, chlorine, bromine or iodine.

The synthesis of the compounds of the invention is outlined on the following flow sheet:

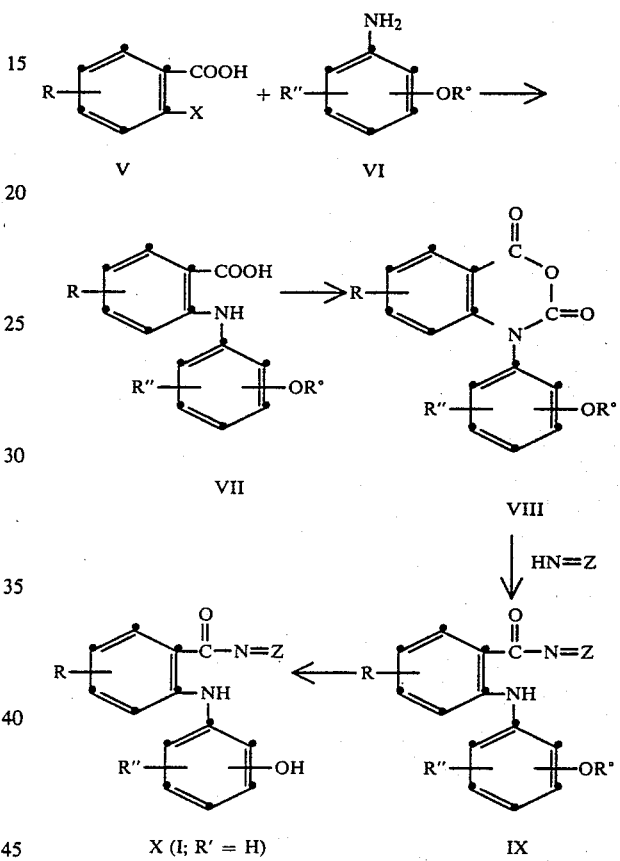

A 2-halobenzoic acid (V, where X is Cl, Br or I) is caused to react with an aminophenol ether (VI), usually in the presence of a catalyst such as cupric acetate, to yield an anthranilic acid derivative of Formula VII. In these formulas, R, R" and R° have the meanings given above, except that when R is alkoxy, R° must be benzyl.

The amino acid of Formula VII is converted to the corresponding isatoic acid anhydride (VIII) by treating the acid VII with ethyl chloroformate or phosgene.

The isatoic anhydride VIII is then reacted with ammonia or an amine, HN=Z to produce a compound of Formula IX. The reaction takes place at room temperature in an inert solvent.

The final step is de-etherification which is carried out by catalytic hydrogenation (R° is benzyl) or by acid treatment (R' is benzyl or lower-alkyl). The hydrogenation takes place at room temperature in an inert solvent in the presence of a conventional hydrogenation catalyst such as palladium-on-carbon. De-etherification by acid treatment is carried out by the action of a strong protonic acid or a Lewis acid, and the reaction takes place under a wide variety of conditions depending upon the reagent used. When a protonic acid is used, moderate heating (50°-150° C.) is generally needed, whereas the reaction using a Lewis acid will take place at ambient temperature or below. Boron tribromide is a preferred reagent.

If a compound of Formula I where R' is lower-alkyl is desired, it can be obtained by N-alkylation of an intermediate of Formula IX, followed by de-etherification. The N-alkylation is effected by means of a lower-alkyl halide (preferably bromide or iodide) in the presence of a strong base such as sodium hydride.

The compounds of Formula II are formed by oxidation of compounds of Formula I where R'=H and the hydroxy group is in the para-position with respect to the nitrogen. The oxidation takes place readily in the presence of oxidizing agents known to convert para-aminophenols to the corresponding 4-imino-2,5-cyclohexadien-1-ones. Such oxidizing agents include elementary oxygen, hydrogen peroxide, organic peroxides, and various salts in a highly oxidized state, such as perchlorates and periodates, or which readily decompose to form elementary oxygen such as mercuric oxide.

The following examples will further illustrate the invention.

EXAMPLE 1

(a) 2-(4-Methoxyphenylamino)benzoic acid [VII; R and R"=H, OR°=4—OCH$_3$].

A mixture of 52 g (0.33 mole) of 2-chlorobenzoic acid, 82 g (0.66 mole) of 4-methoxyaniline, 46 g (0.33 mole) of potassium carbonate, 5 g (0.025 mole) of cupric acetate and 150 ml of dimethylformamide was heated at reflux for two hours. The reaction mixture was cooled, 300 ml of water added and the mixture filtered. The filtrate was acidified with 50 ml of 6N hydrochloric acid, and the resulting solid was collected by filtration and recrystallized from acetonitrile to give 61 g of 2-(4-methoxyphenylamino)benzoic acid.

(b) N-(4-Methoxyphenyl)isatoic anhydride [VIII; R and R"=H, OR°=4—OCH$_3$].

A suspension of 40 g of 2-(4-methoxyphenylamino)benzoic acid in 200 ml of ethyl chloroformate was heated at reflux for 24 hours. The reaction mixture was cooled in an ice-bath and the solid which separated was collected by filtration to give 31 g of N-(4-methoxyphenyl)isatoic anhydride after 6 hours of drying in a vacuum oven. An additional 9 g of product was obtained by concentration of the filtrate in vacuo.

(c) 1-[2-(4-Methoxyphenylamino)benzoyl]piperidine [IX; R and R"=H, OR°=4—OCH$_3$, N=Z=1-piperidinyl].

A mixture of 15 g (0.052 mole) of N-(4-methoxyphenyl)isatoic anhydride and 10 ml (0.11 mole) of piperidine in 50 ml of dimethylformamide was stirred at room temperature for two hours. The reaction mixture was concentrated in vacuo and the residue recrystallized from 75 ml of isopropyl alcohol to give 13.8 g of 1-[2-(4-methoxyphenylamino)benzoyl]piperidine, colorless powder, m.p. 106°-108° C.

(d) 1-[2-(4-Hydroxyphenylamino)benzoyl]piperidine [I; R, R' and R"=H; N=Z=1-piperidinyl, OH at 4-position].

Boron tribromide (10 ml in 25 ml of methylene dichloride) was added dropwise over a 30 minute period to a solution of 15.5 g of 1-[2-(4-methoxyphenylamino)benzoyl]piperidine in 80 ml of dry methylene dichloride cooled in a bath of Dry Ice and isopropyl alcohol. The reaction mixture was allowed to warm to room temperature and to stand overnight. The solvent was then removed in vacuo, and the residue was treated with 100 ml of distilled water and made basic with about 250 ml of saturated sodium bicarbonate solution. The solid which formed was collected by filtration and recrystallized from ethanol to give 10.2 g of 1-[2-(4-hydroxyphenylamino)benzoyl]piperidine, colorless powder, m.p. 199°-201° C.(decompn.).

It is contemplated that the N-methyl derivative of 1-[2-(4-hydroxyphenylamino)benzoyl]piperidine, namely, 1-{2-[methyl-(4-hydroxyphenyl)amino]benzoyl}-piperidine [I; R and R"=H, R'=CH$_3$, N=Z=1-piperidinyl, OH at 4-position] can be prepared by reacting the intermediate of part (c) above first with sodium hydride and then with methyl iodide to obtain 1-{2-[methyl-(4-methoxyphenyl)amino]benzoyl}piperidine [III; R and R"=H, R'=CH$_3$, N=Z=1-piperidinyl, OCH$_3$ at 4-position], and treating the latter with boron tribromide according to the procedure of part (d) above.

EXAMPLE 2

1-{2-[(4-Oxo-2,5-cyclohexadien-1-ylidene)amino]benzoyl}piperidine [II; R and R"=H, N=Z=1-piperidinyl].

A mixture of 8.9 g (0.03 mole) 1-[2-(4-hydroxyphenylamino)benzoyl]piperidine, 6.4 g (0.03 mole) of mercuric oxide, 80 ml of toluene and 20 ml of ethanol was heated at reflux for three hours. The reaction mixture was filtered through an alumina column and eluted with ethyl acetate. The solvent was removed in vacuo and the residue subjected to high pressure liquid chromatography, eluting with 20% ethyl acetate in hexane. The resulting 5.4 g of oil was partitioned between water and ether, the ether fraction dried over anhydrous sodium sulfate and concentrated, and the residue recrystallized from hexane to give 3.1 g of 1-{2-[(4-oxo-2,5-cyclohexadien-1-ylidene)amino]benzoyl}piperidine, orange powder, m.p. 74°-76° C.

It is contemplated that 1-{2-[(4-oxo-2,5-cyclohexadien-1-ylidene)amino]benzoyl}piperidine can alternatively be prepared by treating a methylene dichloride solution of 1-[2-(4-hydroxyphenylamino)benzoyl]piperidine with sodium metaperiodate.

By following the reaction procedures of Example 1, parts (c) and (d), replacing the piperidine in part (c) by molar equivalent amounts of the appropriate HN=Z reactant, there were obtained the following compounds:

EXAMPLE 3

(a) 2-(4-Methoxyphenylamino)benzamide [IX; R and R"=H, OR°=4—OCH$_3$, N=Z=NH$_2$], drab-olive powder, m.p. 178°-180° C.

(b) 2-(4-Hydroxyphenylamino)benzamide [I; R, R' and R"=H, N=Z=NH$_2$, OH at 4-position], m.p. 201° C., olive-green powder from acetonitrile.

EXAMPLE 4

(a) 1-[2-(4-Methoxyphenylamino)benzoyl]pyrrolidine [IX; R and R"=H, OR°=4—OCH$_3$, N=Z=1-pyrrolidinyl], m.p. 119°-120° C., colorless needles from acetonitrile.

(b) 1-[2-(4-Hydroxyphenylamino)benzoyl]pyrrolidine [I; R, R' and R"=H, N=Z=1-pyrrolidinyl, OH at 4-position], m.p. 206°-207° C., colorless plates from methanol.

EXAMPLE 5

(a) 2-(4-Methoxyphenylamino)-N-propylbenzamide [IX; R and R″=H, OR°=4—OCH$_3$, N═Z═NH(CH$_2$)$_2$CH$_3$], colorless powder, m.p. 98°-100° C., after recrystallization from acetonitrile and chromatography on silica using chloroform as eluant.

(b) 2-(4-Hydroxyphenylamino)-N-propylbenzamide [I; R, R′ and R″=H, N═Z═NH(CH$_2$)$_2$CH$_3$, OH at 4-position], m.p. 134°-135° C., pale yellow powder from ethyl acetatehexane

EXAMPLE 6

(a) 1-[2-(4-Methoxyphenylamino)benzoyl]-4-methylpiperidine [IX; R and R″=H, OR°=4—OCH$_3$, N═Z═4-methyl-1-piperidinyl], colorless powder, m.p. 104°-105° C.

(b) 1-[2-(4-Hydroxyphenylamino)benzoyl]-4-methylpiperidine [I; R, R′ and R″=H, N═Z═4-methyl-1-piperidinyl, OH at 4-position], m.p. 143°-145° C., orange-brown powder from ethyl acetate.

EXAMPLE 7

(a) 2-(4-Methoxyphenylamino)-N-methylbenzamide [IX; R and R″=H, OR°=4—OCH$_3$, N═Z═NHCH$_3$], colorless powder, m.p. 112°-113° C. after chromatography on silica using chloroform as eluant.

(b) 2-(4-Hydroxyphenylamino)-N-methylbenzamide [I; R, R′ and R″=H, N═Z═NHCH$_3$, OH at 4-position], m.p. 191°-192° C., light tan powder from ether-ethyl acetate.

EXAMPLE 8

(a) N,N-Diethyl-2-(4-methoxyphenylamino)benzamide [IX; R and R″=H, OR°=4—OCH$_3$, N═Z═N(C$_2$H$_5$)$_2$], tan powder, m.p. 62° C.

(b) N,N-Diethyl-2-(4-hydroxyphenylamino)benzamide [I; R, R′ and R″=H, N═Z═N(C$_2$H$_5$)$_2$, OH at 4-position], m.p. 128°-129° C., colorless powder from ethyl acetate.

EXAMPLE 9

(a) 2-(4-Methoxyphenylamino)-N-isopropylbenzamide [IX; R and R″=H, OR°=4—OCH$_3$, N═Z═NHCH(CH$_3$)$_2$], m.p. 103°-105° C., pale yellow needles from acetonitrile.

(b) 2-(4-Hydroxyphenylamino)-N-isopropylbenzamide [I; R, R′ and R″=H, N═Z═NHCH(CH$_3$)$_2$, OH at 4-position], m.p. 155°-157° C.(decompn.), greyish-pink powder from hexane.

EXAMPLE 10

(a) 2-(4-Methoxyphenylamino)-N,N-dimethylbenzamide [IX; R and R″=H, OR°=4—OCH$_3$, N═Z═N(CH$_3$)$_2$], m.p. 129.5°-130.5° C., colorless crystals from isopropyl alcohol.

(b) 2-(4-Hydroxyphenylamino)-N,N-dimethylbenzamide [I; R, R′ and R″=H, N═Z═N(CH$_3$)$_2$, OH at 4-position], m.p. 198°-199° C., light tan powder from acetonitrile.

EXAMPLE 11

(a) 2-(4-Methoxyphenylamino)-N-benzylbenzamide [IX; R and R″=H, OR°=4—OCH$_3$, N═Z═NHCH$_2$C$_6$H$_5$], m.p. 119°-120° C., light tan powder from acetonitrile.

(b) 2-(4-Hydroxyphenylamino)-N-benzylbenzamide [I; R, R′ and R″=H, N═Z═NHCH$_2$C$_6$H$_5$, OH at 4-position], m.p. 169°-170° C., yellow powder from acetonitrile.

EXAMPLE 12

(a) N-Cyclohexyl-2-(4-methoxyphenylamino)benzamide [IX; R and R″=H, OR°=4—OCH$_3$, N═Z═NH-cyclohexyl], m.p. 144°-146° C., light tan powder from ethyl acetate.

(b) N-Cyclohexyl-2-(4-hydroxyphenylamino)benzamide [I; R, R′ and R″=H, N═Z═NH-cyclohexyl, OH at 4-position], m.p. 225 -227° C., tan powder from acetonitrile.

EXAMPLE 13

(a) 2-(4-Metoxyphenylamino)-N-ethyl-N-methylbenzamide [IX; R and R″=H, OR°=4—OCH$_3$, N═Z═N(CH$_3$)(C$_2$H$_5$)], m.p. 97°-98° C., colorless powder from ethyl acetate.

(b) 2-(4-Hydroxyphenylamino)-N-ethyl-N-methylbenzamide [I; R, R′ and R″=H, N═Z═N(CH$_3$)(C$_2$H$_5$), OH at 4-position], m.p. 162°-164° C., colorless powder from acetonitrile.

EXAMPLE 14

(a) 2-(4-Methoxyphenylamino)-N-ethyl-N-propylbenzamide [IX; R and R″=H, OR°=4—OCH$_3$, N═Z═N(C$_2$H$_5$)(C$_3$H$_7$)].

(b) 2-(4-Hydroxyphenylamino)-N-ethyl-N-propylbenzamide [I; R, R′ and R″=H, N═Z═N(C$_2$H$_5$)(C$_3$H$_7$); OH at 4-position], m.p. 135°-136° C., grey powder from acetonitrile.

EXAMPLE 15

(a) 2-(2-Methoxyphenylamino)benzoic acid [VII; R and R″=H, OR°=2—OCH$_3$].

A mixture of 40 g (0.25 mole) of 2-chlorobenzoic acid, 21 ml (0.26 mole) of 2-methoxyaniline, 3.84 g cupric acetate, 35.4 g of potassium carbonate and 155 ml of dimethylformamide was heated at 120° C. for 12 hours. The reaction mixture was poured into ice-water, acidified with concentrated hydrochloric acid to pH 2, and stirred for one hour. The solid product was collected by filtration, air dried and recrystallized from toluene to give 28.61 g of 2-(2-methoxyphenylamino)-benzoic acid.

(b) N-(2-Methoxyphenyl)isatoic anhydride [VIII; R and R″=H, OR°=2—OCH$_3$].

To a suspension of 24.44 g (0.177 mole) of potassium carbonate in 119 ml of toluene and 238 ml of water, stirred at 20°-40° C., was added 28.61 g (0.1176 mole) of 2-(2-methoxyphenylamino)benzoic acid, and phosgene was bubbled through the mixture for a period of 3.5 hours. The reaction was allowed to stand overnight with stirring, and the solid material was collected by filtration. The latter was dissolved in ethyl acetate and added to the toluene layer separated from the filtrate. The solution was washed twice with 200 ml 1N potassium hydroxide and dried over anhydrous magnesium sulfate. The solvent was removed in vacuo to yield 7 g of N-(2-methoxyphenyl)isatoic anhydride.

(c) 1-[2-(2-Methoxyphenylamino)benzoyl]piperidine [IX; R and R″=H, OR°=2—OCH$_3$, N═Z═1-piperidinyl], m.p. 97°-99° C., light yellow powder from cyclohexane, was prepared from N-(2-methoxyphenyl)isatoic anhydride annd piperidine.

(d) 1-[2-(2-Hydroxyphenylamino)benzoyl]piperidine [I, R, R′ and R″=H, N═Z═1-piperidinyl, OH at 2-position], m.p. 178°-179° C., tan powder from acetonitrile, was prepared by treatment of the methyl ether from part (c) with boron tribromide.

EXAMPLE 16

(a) 2-(4-Benzyloxyphenyl)isatoic anhydride [VIII; R and R''=H, OR°=4—OCH$_2$C$_6$H$_5$] was prepared from 2-(4-benzyloxyphenylamino)benzoic acid and phosgene according to the procedure of Example 15, part (b), and was obtained in the form of a grey solid which was purified by percolation chromatography.

(b) 4-[2-(4-Benzyloxyphenylamino)benzoyl]morpholine [IX; R and R''=H, OR°=4—OCH$_2$C$_6$H$_5$, N=Z=4-morpholinyl], m.p. 101°-103° C., colorless powder from acetonitrile, was prepared from the anhydride of part (a) and morpholine.

(c) 4-[2-(4-Hydroxyphenylamino)benzoyl]morpholine [I; R, R' and R''=H, N=Z=4-morpholinyl, OH at 4-position].

To a warm solution of 16.1 g of 4-[2-(4-benzyloxyphenylamino)benzoyl]morpholine in 300 ml of absolute ethanol containing 2 ml of concentrated hydrochloric acid was added 0.5 g of 10% palladium-on-carbon catalyst, and the mixture was hydrogenated in a Parr apparatus for about four hours. The resulting mixture was filtered and concentrated in vacuo to give 10.5 g of solid product which was recrystallized from acetonitrile to give 5.77 g of 4-[2-(4-hydroxyphenylamino)benzoyl]morpholine, light tan powder, m.p. 214°-216° C.

The same compound can be obtained by boron tribromide treatment of the corresponding methyl ether, 4-[2-(4-methoxyphenylamino)benzoyl]morpholine [IX; R and R''=H, OR°=4—OCH$_2$C$_6$H$_5$, N=Z=4-morpholinyl], m.p. 111°-112° C.

EXAMPLE 17

(a) 5-Chloro-2-(4-methoxyphenylamino)benzoic acid [VII; R=5—Cl, R''=H, OR°=4—OCH$_3$] was prepared from 2,5-dichlorobenzoic acid and 4-benzyloxyaniline according to the procedures of Example 1, part (a).

(b) 5-Chloro-N-(4-methoxyphenyl)isatoic anhydride [VIII; R=5—Cl, R''=H, OR°=4—OCH$_3$] was prepared in 65% yield from the acid of part (a) and ethyl chloroformate by the procedure of Example 1, part (b).

(c) 5-Chloro-N,N-diethyl-2-(4-methoxyphenylamino)benzamide [IX; R=5—Cl, R''=H, OR°=4—OCH$_3$, N=Z=N(C$_2$H$_5$)$_2$], m.p. 75° C., colorless powder from hexane, was prepared from the anhydride of part (b) and diethylamine.

(d) 5-Chloro-N,N-diethyl-2-(4-hydroxyphenylamino)benzamide [I; R=5—Cl, R' and R''=H, N=Z=N(C$_2$H$_5$)$_2$, OH at 4-position], m.p. 173°-174.5° C., light tan powder from ethyl acetate, was prepared from the methyl ether of part (c) and boron tribromide.

EXAMPLE 18

(a) 1-[5-Chloro-2-(4-methoxyphenylamino)benzoyl]piperidine [IX; R=5—Cl, R''=H, OR°=4—OCH$_3$, N=Z=1-piperidinyl], m.p. 92°-93° C. (decompn.), greenish-grey powder from ethyl acetate-hexane, was prepared from 5-chloro-N-(4-methoxyphenyl)isatoic anhydride and piperidine.

(b) 1-[5-Chloro-2-(4-hydroxyphenylamino)benzoyl]piperidine [I; R=5—Cl, R' and R''=H, N=Z=1-piperidinyl, OH at 4-position], m.p. 191°-192° C., orange-pink powder, was prepared from the methyl ether of part (a) and boron tribromide.

EXAMPLE 19

(a) 4-Chloro-2-(4-methoxyphenylamino)benzoic acid [VII; R=4—Cl, R''=H, OR°=4—OCH$_3$] was prepared from 2,4-dichlorobenzoic acid and 4-methoxyaniline according to the procedure of Example 1, part (a), and was obtained in about 60% yield as a green-grey solid.

(b) 4-Chloro-N-(4-methoxyphenyl)isatoic anhydride [VIII; R=4—Cl, R''=H, OR°=4—OCH$_3$] was prepared in about 70% yield from the acid of part (a), and ethyl chloroformate by the procedure of Example 1, part (b).

(c) 1-[4-Chloro-2-(4-methoxyphenylamino)benzoyl]pyrrolidine [IX; R=4—Cl, R''=H, OR°=4—OCH$_3$, N=Z=1-pyrrolidinyl], colorless powder, m.p. 153°-154° C., was prepared from the anhydride of part (b) and pyrrolidine.

(d) 1-[4-Chloro-2-(4-hydroxyphenylamino)benzoyl]pyrrolidine [I; R=4—Cl, R' and R''=H, N=Z=1-pyrrolidinyl, OH at 4-position], m.p. 227°-228° C., light tan powder from aqueous ethanol, was prepared from the methyl ether of part (c) and boron tribromide.

EXAMPLE 20

(a) 1-[4-Chloro-2-(4-methoxyphenylamino)benzoyl]piperidine [IX; R=4—Cl, R''=H, OR°=4—OCH$_3$, N=Z=1-piperidinyl], m.p. 135° C., colorless powder from dimethylformamide, was prepared from 4-chloro-N-(4-methoxyphenyl)isatoic anhydride and piperidine.

(b) 1-[4-Chloro-2-(4-hydroxyphenylamino)benzoyl]piperidine [I; R=4—Cl, R' and R''=H, N=Z=1-piperidinyl, OH at 4-position], m.p. 245°-246° C., colorless powder from ethanol, was prepared from the methyl ether of part (a) and boron tribromide.

EXAMPLE 21

(a) 4-Chloro-2-(4-methoxyphenylamino)-N-methylbenzamide [IX; R=4—Cl, R''=H, OR°=4—OCH$_3$, N=Z=NHCH$_3$], m.p. 131°-132° C., colorless powder from ether, was prepared from 4-chloro-N-(4-methoxyphenyl)isatoic anhydride and methylamine.

(b) 4-Chloro-2-(4-hydroxyphenylamino)-N-methylbenzamide [I; R=4—Cl, R' and R''=H, N=Z=NHCH$_3$, OH at 4-position], m.p. 265°-266° C., light tan powder from aqueous ethanol, was prepared from the methyl ether of part (a) and boron tribromide.

EXAMPLE 22

(a) 2-(4-Benzyloxyphenylamino)-5-methoxybenzoic acid [VII; R=5—CH$_3$O, R''=H, OR°=4—OCH$_2$C$_6$H$_5$].

To a 5 L 3-neck flash was added 284 g (2.06 moles) milled potassium carbonate and 1.0 L dimethylformamide. While stirring the resulting mixture at room temperature, 250 g (1.06 moles) 4-benzyloxyaniline hydrochloride was added portionwise over 15 minutes. After this was completed, 231 g (1.0 mole) 2-bromo-5-methoxybenzoic acid was added over 15 minutes and the mixture was stirred for another 15 minutes. The suspension was cooled to 10°-15° C. and 13.8 g cupric acetate monohydrate (0.06 moles) was added portionwise over 20 minutes. Gas evolved slowly and after stirring 15 minutes at room temperature the reaction was warmed on a steam bath over 40 minutes to 70° C. whereupon a vigorous evolution of carbon dioxide was observed. Stirring and heating was continued for 90 minutes at 80°-85° C., heat was removed and the mixture was allowed to cool to room temperature. The brownish red suspension was transferred to a 12 L flask containing 1 L ice-cold water. Acetic acid (650 ml) was added dropwise and the dark green precipitate was stirred vigorously until homogeneous. After filtering and washing well with water, the crude product was dried overnight at 55°–60° C. in a vacuum oven. The crude product (approximately 350 g) was diluted with 5.8 L toluene, heated to reflux temperature and filtered. The dark green filtrate was allowed to cool to room temperature for 2–3 hours, and the solid product was collected by filtration and rinsed with cold (5°–10° C.) toluene. The bright yellow crystalline product was obtained in 80% yield. A sample of the compound had the m.p. 167°–168° C. when recrystallized from a benzene-cyclohexane mixture.

(b) N-(4-Benzyloxyphenyl)-5-methoxyisatoic anhydride [VIII; $R=5-CH_3O$, $R''=H$, $OR°=4-OCH_2C_6H_5$] was prepared from 2-(4-benzyloxyphenylamino)-5-methoxybenzoic acid and phosgene according to the procedure of Example 1, part (b), and was obtained in 79% yield as a colorless solid used directly in the next reaction.

(c) 2-(4-Benzyloxyphenylamino)-N-benzyl-5-methoxybenzamide [IX; $R=5-CH_3O$, $R''=H$, $N=Z=NHCH_2C_6H_5$, $OR°=4-OCH_2C_6H_5$], m.p. 83°–84° C., pale yellow solid from ether, was prepared from the anhydride of part (b) and benzylamine.

(d) 2-(4-Hydroxyphenylamino)-N-benzyl-5-methoxybenzamide [I; $R=5-CH_3O$, $R'$ and $R''=H$, $N=Z=NHCH_2C_6H_5$, OH at 4-position], m.p. 160°–161° C., yellow powder from acetonitrile, was prepared by catalytic hydrogenation of the benzyl ether of part (c) according to the procedure of Example 16(c).

EXAMPLE 23

(a) 1-[5-Methoxy-2-(4-benzyloxyphenylamino)benzoyl]piperidine [IX; $R=5-CH_3O$, $R''=H$, $N=Z=1$-piperidinyl, $OR°=4-OCH_2C_6H_5$], m.p. 91°–92° C., light tan solid from cyclohexane, prepared from the anhydride of Example 22(b) and piperidine.

(b) 1-[2-(4-Hydroxyphenylamino)-5-methoxybenzoyl]piperidine [I; $R=5-CH_3O$, $R'$ and $R''=H$, $N=Z=1$-piperidinyl, OH at 4-position], m.p. 118°–120° C., pale tannish-yellow powder from ether, prepared by catalytic hydrogenation of the benzyl ether of part (a).

EXAMPLE 24

(a) 2-(3-Benzyloxyphenylamino)benzoic acid [VII; R and $R''=H$, $OR°=3-OCH_2C_6H_5$] was prepared from 2-chlorobenzoic acid and 3-benzyloxyaniline according to the procedure of Example 1(a). The green solid obtained was used directly in the next reaction.

(b) N-(3-Benzyloxyphenyl)isatoic anhydride [VIII; R and $R''=H$, $OR°=3-OCH_2C_6H_5$] was prepared from the acid of part (a) and ethyl chloroformate according to the procedure of Example I, part (b). It was obtained in the form of a light tan solid, m.p. 155° C.

(c) 1-[2-(3-Benzyloxyphenylamino)benzoyl]piperidine [IX; R and $R''=H$, $N=Z=1$-piperidinyl, $OR°=3-OCH_2C_6H_5$], grey granules, m.p. 90°–91° C., was prepared from the anhydride of part (b) and piperidine.

(d) 1-[2-(3-Hydroxyphenylamino)benzoyl]piperidine [I; R, $R'$ and $R''=H$, $N=Z=1$-piperidinyl, OH at 3-position], m.p. 142°–143° C., tan powder from aqueous methanol, was prepared by catalytic hydrogenation of the benzyl ether of part (c).

EXAMPLE 25

2-(4-Methoxy-2-methylphenylamino)benzoic acid [VII; $R=H$, $R''=2-CH_3$, $OR°=4-OCH_3$] was prepared from 2-chlorobenzoic acid and 4-methoxy-2-methylaniline according to the procedure of Example 1(a), and was obtained in 59% yield as a grey solid.

It is contemplated that the foregoing product by reaction with phosgene or ethyl chloroformate can be converted to N-(4-methoxy-2-methylphenyl)isatoic anhydride [VIII; $R=H$, $R''=2-CH_3$, $OR°=4-OCH_3$], and the latter reacted with piperidine to give 1-[2-(4-methoxy-2-methylphenylamino)benzoyl]piperidine [IX; $R=H$, $R''=2-CH_3$, $N=Z=1$-piperidinyl, $OR°=4-OCH_3$] which can be de-etherified with boron tribromide to yield 1-[2-(4-hydroxy-2-methylphenylamino)benzoyl]piperidine [I; R and $R'=H$, $R''=2-CH_3$, $N=Z=1$-piperidinyl, OH at 4-position].

EXAMPLE 26

2-(3-Chloro-4-methoxyphenylamino)benzoic acid [VII; $R=H$, $R''=3-Cl$, $OR°=4-OCH_3$] was prepared from 2-chlorobenzoic acid and 3-chloro-4-methoxyaniline according to the procedure of Example 1, part (a), and was obtained in 68% yield as a solid recrystallized from acetonitrile.

It is contemplated that the foregoing product by reaction with phosgene and ethyl chloroformate can be converted to N-(3-chloro-4-methoxyphenyl)isatoic anhydride [VIII; $R=H$, $R''=3-Cl$, $OR°=4-OCH_3$], and the latter reacted with piperidine to give 1-[2-(3-chloro-4-methoxyphenylamino)benzoyl]piperidine [IX; $R=H$, $R''=3-Cl$, $N=Z=1$-piperidinyl, $OR°=4-OCH_3$] which can be de-etherified with boron tribromide to yield 1-[2-(3-chloro-4-hydroxyphenylamino)benzoyl]piperidine [I; R and $R'=H$, $R''=3-Cl$, $N=Z=1$-piperidinyl, OH at 4-position].

EXAMPLE 27

It is contemplated that N-(4-methoxyphenyl)isatoic anhydride (Example 1c) can be caused to react with N-benzyl-N-methylamine to produce 2-(4-methoxyphenylamino)-N-benzyl-N-methylbenzamide [IX; R and $R''=H$, $OR°=4-OCH_3$, $N=Z=N(CH_3)CH_2C_6H_5$], and the latter de-etherified with boron tribromide to yield 2-(4-hydroxyphenylamino)-N-benzyl-N-methylbenzamide [I; R, $R'$ and $R''=H$, $N=Z=N(CH_3)CH_2C_6H_5$, OH at 4-position].

The compounds of Formulas I and II have been found to inhibit lipoxygenase activity in biological systems, thus indicating their usefulness as anti-asthmatic agents.

Slow reacting substance of anaphylaxis (SRS-A) is a descriptive term for a family of lipoxygenase metabolic products of arachidonic acid designated as the leukotrienes. These substances are potent contractile agents of vascular and pulmonary smooth muscle. The relationship of SRS-A to asthma was first characterized by Brockelhurst [Rev. in Adv. Drug Res. 19, 109 (1970)] who identified the material as being present subsequent to specific antigen challenge of living tissue obtained from asthmatic patients. Herxheimer and Stressmann [J. Physiol. 165, 78P (1953)] first demonstrated that aerosolized guinea pig SRS-A induced bronchospasm in man. This observation has been more recently confirmed using purified leukotrienes.

Recent studies have indicated that lipoxygenase inhibiting compounds may have therapeutic potential in treating diseased states other than asthma, e.g. bronchitis, acute inflammation, arthritis, psoriasis, cardiovascular insufficiency and myocardial infarct.

The primary screening test used is a determination of the inhibition of lipoxygenase and cyclooxygenase derived from rat basophilic leukemia (RBL-1) cells. The test was carried out according to the following procedure:

Single cell suspensions of RBL-1 cells are homogenized to obtain the microsomal fraction containing lipoxygenase and cyclooxygenase. Test compounds are added to the enzyme-containing homogenate for a 5 min preincubation period at 37° C. prior to the addition of $^{14}C$-arachidonic acid substrate. Following incubation at 37° C. for 15 min, the reaction is stopped by the addition of 2M formic acid and the enzyme-substrate products are extracted into chloroform. An aliquot of the extract is evaporated to dryness, reconstituted in ether to 1/10 original volume, spotted in thin layer chromatography plates and chromatographed. The peak areas of radioactivity representing the products are located by scanning the plates. The quantity of products formed is estimated by measuring the height of the radioactivity peaks observed on the chromatographic scans. Alternatively, the areas of radioactivity are scraped from the plate and the $^{14}C$ quantitated by scintillation counting. The percent inhibition in the formation of the cyclooxygenase product PGD2, designated as C1 and lipoxygenase products, L1 designated for 5,12-di-HETE and L2 for 5-HETE are shown. Compounds with >50% inhibition of L1 and L2 at a screening concentration of 1 μM are considered active enough for further investigation.

The following Table summarizes the results obtained from the testing of specific compounds of the invention by the foregoing method.

| Example No. | % Inhibition[a] | IC$_{50}$[b] |
|---|---|---|
| 1[d] | C1 0 | >100 |
| | L1 19 | 3.5 |
| | L2 64 | 0.6 |
| 2 | C1 0 | >1 |
| | L1 68 | 0.45 |
| | L2 82 | 0.13 |
| 3[b] | C1 14 | >1 |
| | L1 78 | 0.31 |
| | L2 83 | 0.15 |
| 4[b] | C1 0 | |
| | L1 41 | |
| | L2 52 | |
| 5[b] | C1 6 | >1 |
| | L1 62 | 0.13 |
| | L2 85 | 0.11 |
| 6[b] | C1 7 | |
| | L1 54 | |
| | L2 77 | |
| 7[b] | C1 2 | |
| | L1 23 | |
| | L2 48 | |
| 8[b] | C1 0 | |
| | L1 33 | |
| | L2 63 | |
| 9[b] | C1 0 | |
| | L1 72 | |
| | L2 78 | |
| 10[b] | C1 1 | |
| | L1 34 | |
| | L2 56 | |
| 11[b] | C1 0 | >1 |
| | L1 87 | 0.07 |
| | L2 96 | 0.04 |
| 12[b] | C1 0 | >1 |
| | L1 80 | 0.12 |
| | L2 94 | 0.11 |
| 13[b] | C1 0 | |
| | L1 66 | |
| | L2 77 | |
| 14[b] | C1 0 | >1 |
| | L1 78 | 0.18 |
| | L2 95 | 0.11 |
| 15[d] | C1 2 | >1 |
| | L1 58 | 0.72 |
| | L2 80 | 0.18 |
| 16[c] | C1 1 | |
| | L1 37 | |
| | L2 42 | |
| 17[d] | C1 0 | |
| | L1 56 | |
| | L2 73 | |
| 18[b] | C1 16 | |
| | L1 63 | |
| | L2 75 | |
| 19[d] | C1 7 | |
| | L1 24 | |
| | L2 42 | |
| 20[b] | C1 12 | |
| | L1 32 | |
| | L2 44 | |
| 21[b] | C1 | >1 |
| | L1 | 0.36 |
| | L2 | 0.18 |
| 22[d] | C1 0 | >1 |
| | L1 81 | 0.30 |
| | L2 97 | 0.26 |
| 23[b] | C1 19 | >1 |
| | L1 89 | 0.54 |
| | L2 96 | 0.61 |
| 24[d] | C1 42[c] | |
| | L1 47[c] | |
| | L2 56[c] | |

[a]Percent inhibition of cyclooxygenase (C1) and lipoxygenase (L1 and L2) formation at a dose of 1 μM.
[b]Inhibitory concentration (μM) in 50% of tests.
[c]Dose of 10 μM.

In vivo activity was measured by the effect on the SRS-A component of immunologically induced broncho-constriction in guinea pigs. The test was carried out according to the following procedure:

Two weeks after immunization with egg albumin, guinea pigs are prepared for bronchoconstriction determination. One hour prior to antigen challenge, each animal is dosed orally with indomethacin and chlorpheniramine. Animals are anesthetized with sodium pentobarbital, the trachea cannulated and the animal artifically respired. Arachidonic acid is administered intravenously prior to antigen challenge. The resulting bronchoconstriction is recorded by the standard lung overflow procedure and the peak increase in intratracheal pressure (mm Hg) over a 10 minute observation period is recorded. Compounds are evaluated for their ability to prevent the increased intratracheal pressure in an experimental group of animals as compared to the medicated (indomethacin+chlorpheniramine+arachidonic acid) control group. The results are expressed in terms of percent inhibition or as ED$_{50}$ values (effective dose in 50% of the animals).

When tested by the foregoing in vivo procedure the compound of Example 1(d), when administered intravenously, caused 48% inhibition when tested at the highest soluble dose (0.1 mg/kg); and the compound of Example 11(b) had ED$_{50}$=0.61 mg/kg (intravenous).

The intermediate alkyl and benzyl ethers of Formulas III and IX were devoid of any significant lipoxygenase inhibiting activity.

The compounds of the invention can be prepared for use by conventional pharmaceutical procedures: that is, by dissolving or suspending them in a pharmaceutically acceptable vehicle, e.g., water, aqueous alcohol, glycol, oil solution or oil-water emulsion, for parenteral or oral administration; or by incorporating them in unit dosage form as capsules or tablets for oral administration either alone or in combination with conventional adjuvants or excipients, e.g., calcium carbonate, starch, lactose, talc, magnesium stearate, gum acacia, and the like.

I claim:

1. A compound of the formula

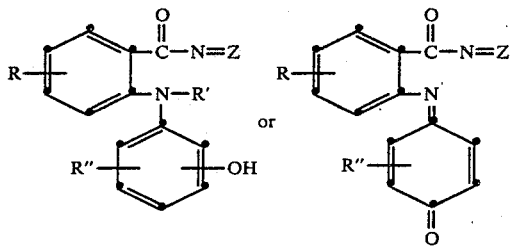

wherein:

R is hydrogen, lower-alkyl, halo or lower-alkoxy;

R' is hydrogen or lower-alkyl;

R" is hydrogen, lower-alkyl or halo; and

N=Z is a member of the group consisting of amino, alkylamino having from one to four carbon atoms, dialkylamino having from two to eight carbon atoms, benzylamino, N-benzyl-N-alkylamino having from eight to ten carbon atoms, 5- or 6-ring-membered cycloalkylamino having from five to eight carbon atoms, 1-pyrrolidinyl, 1-piperidinyl, 4-morpholinyl, and lower-alkylated derivatives of said heterocyclic members.

2. A compound according to claim 1 of the formula

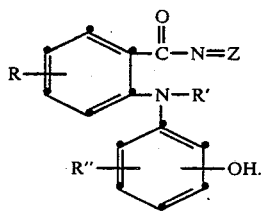

3. 1-[2-(2-Hydroxyphenylamino)benzoyl]piperidine, according to claim 2.

4. A compound according to claim 2 of the formula

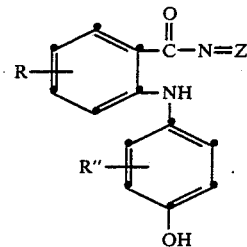

5. 1-[2-(4-Hydroxyphenylamino)benzoyl]piperidine, according to claim 4.

6. 2-(4-Hydroxyphenylamino)benzamide, according to claim 4.

7. 2-(4-Hydroxyphenylamino)-N-propylbenzamide, according to claim 4.

8. 4-Chloro-2-(4-hydroxyphenylamino)-N-methylbenzamide, according to claim 4.

9. 2-(4-Hydroxyphenylamino)-N-benzylbenzamide, according to claim 4.

10. N-Cyclohexyl-2-(4-hydroxyphenylamino)benzamide, according to claim 4.

11. 2-(4-Hydroxyphenylamino)-N-ethyl-N-propylbenzamide, according to claim 4.

12. 1-[2-(4-Hydroxyphenylamino)-5-methoxybenzoyl]piperidine, according to claim 4.

13. 2-(4-Hydroxyphenylamino)-N-benzyl-5-methoxybenzamide, according to claim 4.

14. A compound according to claim 1 of the formula

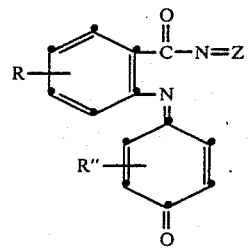

15. 1-{2-[(4-Oxo-2,5-cyclohexadien-1-ylidene)amino]benzoyl}piperidine, according to claim 14.

16. A composition for inhibiting lipoxygenase activity which comprises a pharmacologically effective amount of a compound according to claim 1 together with one or more pharmaceutically acceptable excipients or diluents.

17. A method for inhibiting lipoxygenase activity in a mammal which comprises administering to said mammal a pharmacologically effective amount of a composition according to claim 16.

18. A method for treating or preventing allergic asthma in a mammal which comprises administering to said mammal an anti-asthmatically effective amount of a composition according to claim 16.

* * * * *